United States Patent
Hansen

(10) Patent No.: US 7,230,084 B2
(45) Date of Patent: Jun. 12, 2007

(54) THERAPEUTIC USING A BISPECIFIC ANTIBODY

(75) Inventor: Hans J. Hansen, Picayune, MS (US)

(73) Assignee: Immunomedics, Inc., Morris Plains, NJ (US)

( * ) Notice: Subject to any disclaimer, the term of this patent is extended or adjusted under 35 U.S.C. 154(b) by 415 days.

(21) Appl. No.: 10/259,853

(22) Filed: Sep. 30, 2002

(65) Prior Publication Data

US 2003/0103982 A1  Jun. 5, 2003

Related U.S. Application Data

(62) Division of application No. 09/314,135, filed on May 19, 1999, now Pat. No. 6,458,933.

(60) Provisional application No. 60/086,133, filed on May 20, 1998.

(51) Int. Cl.
C07K 16/00 (2006.01)

(52) U.S. Cl. ............... 530/387.3; 530/387.1; 530/387.7

(58) Field of Classification Search ............. 530/387.3, 530/387.7, 387.1
See application file for complete search history.

(56) References Cited

U.S. PATENT DOCUMENTS

| | | |
|---|---|---|
| 3,927,193 A | 12/1975 | Hansen et al. |
| 4,331,647 A | 5/1982 | Goldenberg |
| 4,348,376 A | 9/1982 | Goldenberg |
| 4,361,544 A | 11/1982 | Goldenberg |
| 4,460,561 A | 7/1984 | Goldenberg |
| 4,468,457 A | 8/1984 | Goldenberg et al. |
| 4,624,846 A | 11/1986 | Goldenberg |
| 4,671,958 A | 6/1987 | Rodwell et al. |
| 4,699,784 A | 10/1987 | Shih et al. |
| 4,818,709 A | 4/1989 | Primus et al. |
| 4,925,648 A | 5/1990 | Hansen et al. |
| 4,932,412 A | 6/1990 | Goldenberg |
| 6,018,031 A | 1/2000 | Shen et al. |

FOREIGN PATENT DOCUMENTS

| | | |
|---|---|---|
| EP | 0 308 208 | 3/1989 |
| EP | 0 308 208 A1 * | 3/1989 |
| WO | WO 92/19273 | 11/1992 |
| WO | WO 97/23237 | 7/1997 |

OTHER PUBLICATIONS

Hansen, et al. Internalization and Catabolism of radiolabelled antibodies to the MHC class-II invatiant chain by B-cell lymphomas. Biochem. Journal 1996 ol 320, pp. 293-300.*
Hansen, *Biochem. J.* (1996), vol. 320, pp. 293-300.
Cardenas et al., *Infection and Immunity* (1993), vol. 61, pp. 4629-4636.
Hosmalin et al., *PNAS* (1990), vol. 87, pp. 2344-2348.
Hansen et al., Internalization and Catabolism of Radiolabelled Antibodies to the MHC Class-II Invariant Chain by 8-Cell Lymphmas, *Biochemical Journal* (Nov. 15, 1996), vol. 320, pp. 293-300, XP-002110872.
Gautherot et al., "Therapy for Colon Carcinoma Xenografts with Bispecific Antibody-Targeted, Lodine-131-Labeled Bivalent Hapten," *Cancer* (Dec. 15, 1997), vol. 80, pp. 2618-2623, XP-002110873.
Karacay et al., "Development of a Streptavidin-anti-Carcinoembyronic Antigen Antibody, Readiolabeled Biotin Pretargeting Method for Radioimmunotherapy of Colorectal Cancer. Reagent Development," *Bioconjugate Chemistry* (Jul.-Aug. 1997), vol. 8, No. 4, pp. 585-594, XP-002110874.
Elsasser, David, et al., "HLA Class II as Potential Target Antigen on Malignant B Cells for Therapy with Bispecific Antibodies in Combination with Granulocyte Colony-Stimulating Factor" Blood, vol. 87, No. 9 (May 1, 1996: pp. 3803-3812.
Mezzanzanica, Delia, et al., "Retargeting of Human Lymphocytes Against Human Ovarian Carcinoma Cells by Bispecific Antibodies: from laboratory to Clinic" Int. J. Clin. Lab Res 21:159-164, 1991.

* cited by examiner

*Primary Examiner*—Bruce R. Campell
*Assistant Examiner*—Myron G. Hill
(74) *Attorney, Agent, or Firm*—Faegre & Benson LLP

(57) ABSTRACT

Multivalent, multispecific molecules having at least one specificity for a pathogen and at least one specificity for the HLA class II invariant chain (Ii) are administered to induce clearance of the pathogen. In addition to pathogens, clearance of therapeutic or diagnostic agents, autoantibodies, anti-graft antibodies, and other undesirable compounds may be induced using the multivalent, multispecific molecules.

9 Claims, No Drawings

THERAPEUTIC USING A BISPECIFIC ANTIBODY

This is the application claims benefit of priority to U.S. Ser. No. 09/314,135 filed May 19, 1999, now U.S. Pat. No. 6,458,933, which claims the benefit under 35 U.S.C. §119(e) to U.S. Provisional Patent Application No. 60/086,133, filed May 20, 1998.

BACKGROUND OF THE INVENTION

Most forms of nonsurgical cancer therapy, such as external irradiation and chemotherapy, are limited in their efficacy because of toxic side effects to normal tissues and cells, because of the limited specificity of these treatment modalities for cancer cells. This limitation is also of importance when anti-cancer antibodies are used for targeting toxic agents, such as isotopes, drugs, and toxins, to cancer sites, because, as systemic agents, they also circulate to sensitive cellular compartments such as the bone marrow. In acute radiation injury, destruction of lymphoid and hematopoietic compartments is a major factor in the development of septicemia and subsequent death.

In the field of organ transplantation, the recipient's cellular immune response to the foreign graft is depressed with cytotoxic agents which affect the lymphoid and other parts of the hematopoietic system. Graft acceptance is limited by the tolerance of the recipient to these cytotoxic chemicals, many of which are similar to the anticancer (antiproliferative) agents. Likewise, when using cytotoxic antimicrobial agents, particularly antiviral drugs, or when using cytotoxic drugs for autoimmune disease therapy, e.g., in treatment of systemic lupus erythematosis, a serious limitation is the toxic effects to the bone marrow and the hematopoietic cells of the body.

The detection of a target site benefits from a high signal-to-background ratio of detection agent. Therapy benefits from as high an absolute accretion of therapeutic agent at the target site as possible, as well as a reasonably long duration of uptake and binding. In order to improve the targeting ratio and amount of agent delivered to a target site, the use of targeting vectors comprising diagnostic or therapeutic agents conjugated to a targeting moiety for preferential localization has long been known.

Examples of targeting vectors include diagnostic or therapeutic agent conjugates of targeting moieties such as antibody or antibody fragments, cell- or tissue-specific peptides, and hormones and other receptor-binding molecules. For example, antibodies against different determinants associated with pathological and normal cells, as well as associated with pathogenic microorganisms, have been used for the detection and treatment of a wide variety of pathological conditions or lesions. In these methods, the targeting antibody is directly conjugated to an appropriate detecting or therapeutic agent as described, for example, in Hansen et al., U.S. Pat. No. 3,927,193 and Goldenberg, U.S. Pat. Nos. 4,331,647, 4,348,376, 4,361,544, 4,468,457, 4,444,744, 4,460,459, 4,460,561, 4,624,846 and 4,818,709, the disclosures of all of which are incorporated herein by reference.

One problem encountered in direct targeting methods, i.e., in methods wherein the diagnostic or therapeutic agent (the "active agent") is conjugated directly to the targeting moiety, is that a relatively small fraction of the conjugate actually binds to the target site, while the majority of conjugate remains in circulation and compromises in one way or another the function of the targeted conjugate. In the case of a diagnostic conjugate, for example, a radioimmunoscintigraphic or magnetic resonance imaging conjugate, non-targeted conjugate which remains in circulation can increase background and decrease resolution. In the case of a therapeutic conjugate having a very toxic therapeutic agent, e.g., a radioisotope, drug or toxin, attached to a long-circulating targeting moiety such as an antibody, circulating conjugate can result in unacceptable toxicity to the host, such as marrow toxicity or systemic side effects.

While some agents exist for clearing non-interacting agents, these agents do not generally involve the use of a specific mechanism for targeting clearance. In some cases, however, to speed up this hepatobiliary recognition process, the clearing agent may be substituted with sugar residues, primarily galactose, such that the galactosylated complex is recognized by the asialoglycoprotein receptors in the liver. By using a galactosylated biotin-protein, substantially all circulating streptavidin-antibody and galactosylated biotin-protein is deposited into the liver on the first pass through, making the clearing process very fast and efficient. With circulating avidin conjugate removed, excess biotin-chelate-radionuclide is rapidly eliminated, preferably renally. Because the radionuclide spends a very short time in circulation, considerably less marrow toxicity to the patient is seen compared to when the radionuclide is attached directly to the antibody. However, it has been found that some of these clearing agents may bind to and remove the therapeutic or diagnostic agent that is beneficially bound to the target site.

U.S. Pat. No. 4,782,840 discloses a method for reducing the effect of elevated background radiation levels during surgery. The method is to inject the patient with antibodies specific for neoplastic tissue and which are labeled with radioisotopes having a suitably long half-life, such as Iodine-125. After injection of the radiolabeled antibody, the surgery is delayed at least 7-10 days, preferably 14-21 days, to allow any unbound radiolabeled antibody to be cleared to a low bloodpool, background level.

U.S. Pat. No. 4,932,412 discloses methods for reducing or correcting for non-specific background radiation during intraoperative detection. The methods include the administration to a patient who has received a radiolabeled primary antibody, of a contrast agent, subtraction agent or second antibody which binds the primary antibody.

A need exists, therefore, for improved clearing agents which work efficiently and rapidly to target the agent sought to be cleared to the cells responsible for clearance.

SUMMARY OF THE INVENTION

It is one object of the invention to provide multivalent molecules which are suitable for pharmaceutical applications that induce clearance of a variety of noxious substances. According to this and other objects of the invention, a multivalent molecule is provided which has at least one specificity for a noxious substance, such as a pathogenic organism, and at least one specificity for the HLA class II invariant chain (Ii). In one embodiment of the invention, the multivalent molecule is a multispecific antibody molecule. In another embodiment, at least one specificity is directed to a microorganism, such as a fungus. In still other embodiments, the pathogenic organism may be a cancer cell, a parasite or a virus, such as HIV. Further embodiments include pharmaceutical compositions of these multivalent molecules.

Another object of the invention is to provide multivalent molecules that are useful in treating sepsis. According to this an other objects of the invention, a multivalent molecule is provided which has at least one specificity for lipopolysaccharide (LPS) or lymphotoxin and at least one specificity for the HLA class II invariant chain (Ii). Pharmaceutical compositions are also provided.

Another object of the invention is to provide multivalent molecules that are useful in inducing clearance of excess diagnostic or therapeutic agents. According to this and other objects of the invention, a multivalent molecule is provided which has at least one specificity for a diagnostic or therapeutic agent and at least one specificity for the HLA class II invariant chain (Ii). Pharmaceutical compositions are also provided.

Another object of the invention is to provide multivalent molecules that are useful in inducing clearance of autoantibodies. According to this and other objects of the invention, a multivalent molecule is provided which has at least one specificity for a specific binding site of an autoantibody and at least one specificity for the HLA class II invariant chain (Ii).

Another object of the invention is to provide methods of treating a patient exposed to a pathogenic organism. The invention thus provides methods involving administering to the patient an effective amount of a multivalent molecule having at least one specificity for the pathogenic organism and at least one specificity for the HLA class II invariant chain (Ii). In different embodiments, the pathogenic organism is a cancer cell, a parasite or an infectious agent.

A further object of the invention is to provide methods of treating septic shock. According to this object, a method is provided for treating or preventing septic shock, which comprises administering to a patient an effective amount of a multivalent molecule having at least one specificity for lipopolysaccharide (LPS) or lymphotoxin and at least one specificity for the HLA class II invariant chain (Ii).

Still another object of the invention is to provide a method of inducing clearance of an excess diagnostic or therapeutic agent. According to this object, there is provided a method of inducing clearance of a therapeutic or diagnostic agent in a patient, in involves administering to the patient a multivalent molecule having at least one specificity for the agent and at least one specificity for the HLA class II invariant chain (Ii).

DETAILED DESCRIPTION

The invention relates, in general terms, to inducing clearance of a variety of noxious substances from the body. In one aspect of the invention, there is provided a multivalent therapeutic agent, which has at least two different binding specificities. A representative therapeutic agent contains at least one binding specificity for a noxious substance sought to be cleared and at least one specificity to the HLA class II invariant chain (Ii). In another aspect of the invention, there are provided methods of using these therapeutic agents to induce clearance in a patient.

Due to the multiple specificities of the subject therapeutic agents, it is likely that the inventive methods work by forming a bridge between the agent(s) sought to be cleared from the patient and HLA class II molecules. The resulting proximal association, in some manner, is believed to induce or facilitate internalization of the target agent, transportation into lysosomes and degradation of the agent therein.

As used herein "clearance" refers not only to the process of removing the target substance from the body, but also to earlier stages of this process. Clearance also refers to the sequestration of the target substance followed by the removal of the target from, for example, the circulation, lymphatic system, interstitial spaces and the body cavities.

Therapeutic Agents

The therapeutic agents of the invention are multivalent and multispecific. By "multivalent" it is meant that the subject agents may bind more than one target, which may have the same or a different structure, simultaneously. A "target" is either the HLA class II invariant chain or an agent sought to be cleared. By "multispecific" it is meant that the subject agents may bind simultaneously to at least two targets which are of different structure. For example, an agent having one specificity for HLA class II invariant chain and one other specificity for a pathogenic bacterium would be considered multivalent and multispecific because it can bind two structurally different targets simultaneously. On the other hand, a molecule having two specificities for HLA class II invariant chain, but no other specificities, would be multivalent but not multispecific.

Some preferred agents are bispecific, but in some cases additional specificities, e.g. two to six, are preferred. Similarly, some preferred agents are bivalent, but increasing the valency of the agent would be beneficial in binding either additional molecules of the same target or multiple different targets. On preferred class of agents, therefore is bispecific and is at least trivalent, having at least one binding site for Ii and two for the target molecule.

As indicated above, preferred therapeutic agents have at least one specificity directed to HLA class II invariant chain. This specificity confers on the therapeutic agent the characteristic of targeting to invariant chain-positive cells in many organs, such as liver, marrow, spleen, lymph nodes and skin. This targeting is associated with rapid clearance of the therapeutic agent containing this invariant chain specificity through internalization, transport to lysosomes, and subsequent degradation.

The at least one other specificity of the present therapeutic agents may be directed to nearly any substance which it is desirable to have cleared from the body. These substances may be, for example, toxins, pathogenic organisms (e.g., bacteria, fungi, and parasites), viruses, autoantibodies and chemotherapeutic agents. In one embodiment, the pathogenic organism is a fungus of the genus *Cryptococcus*, and especially *Cryptococcus neoformans*.

In another embodiment, the pathogenic organism to be cleared is a cancer cell. The cancer cell will be bound to a phagocytic cell expressing HLA class II invariant chain, which may be a macrophage, Kuppfer cell, or histiocyte, for example, with the subsequent destruction of the cancer cell by the phagocytic cell. Although the cancer cell may be internalized by the phagocytic cell, the cancer cell may first be killed by necrotic or apoptoic induction. The tumor-targeting moiety of the multispecific agent may be an antibody reactive with a tumor associated or tumor specific antigen.

Another substance which is desirable to have cleared from the body is an "autoantibody," an antibody that recognizes a native epitope. Autoantibodies may form immune complexes with normal cells or serum components, leading to their damage or clearance by the immune system, just as immune complexes with foreign pathogens. One source of tissue damage is activation of the complement system. Most antibodies, including autoantibodies, have a site on the Fc portion of the immunoglobulin chain that can react with activated C1q or C3 components of the complement system. Complex formation between the autoantibody, activated C1q or C3, and the cellular surface initiates a cascading activation of other complement components, leading to the damage or destruction of the cell to which the autoantibody is bound.

Among such tumor-associated markers are those disclosed by Herberman, "Immunodiagnosis of Cancer", in Fleisher (ED.), "The Clinical Biochemistry of Cancer", page 347 (Am. Assn. Clin. Chem. 1979) and in U.S. Pat. No. 4,150,149 to Wolfsen et al. Tumor-associated markers have been categorized by Herberman, supra, in a number of categories including oncofetal antigens, placental antigens, oncogenic or tumor virus-associated antigens, tissue-associated antigens, organ-associated antigens, ectopic hormones and normal antigens or variants thereof. Occasionally, a sub-unit of a tumor-associated marker is advantageously used to raise antibodies having higher tumor-specificity, e.g., the beta-subunit of human chorionic gonadotropin (HCG), which stimulates the production of antibodies having a greatly reduced cross-reactivity to non-tumor substances. Suitable such marker substances to which specific antibodies may be raised which are useful in the present invention include, but are not limited to, alpha-fetoprotein (AFP), human chorionic gonadotropin (HCG) and/or its beta-subunit (HCG-beta), colon-specific antigen-p (CSAp), prostatic acid phosphatase, pancreatic oncofetal antigen, placental alkaline phosphatase, pregnancy $beta_1$-globulin, parathormone, calcitonin, tissue polypeptide antigen, T-antigen, $beta_2$-microglobulin, mammary tumor-associated glycoproteins (MTGP), galactyosyl transferase-II (GT-II), gp-52 viral-associated antigen, ovarian cystadenocarcinoma-associated antigen (OCAA), ovarian tumor-specific antigen (OCA), cervical cancer antigens (CA-58, CCA, TA-4), basic fetoprotein (BFP), terminal deoxynucleotidyl transferase (TdT), cytoplasmic melanoma-associated antigens, human astrocytoma-associated antigen (HAAA), common glioma antigen (CGA), glioembryonic antigen (GEA), glial fibrillary acidic protein (GFA), common meningioma antigen (CMA), ferritin, and tumor angiogenesis factor (TAF).

As a result, autoantibodies are responsible for a large number of serious, sometimes life threatening, diseases. Beeson (1994) Am. J. Med. 96:457. For example, autoantibodies may recognize the acetylcholine receptors found in neural muscular junctions, for example. The resulting damage to muscular tissue leads to the development of myasthenia gravis. If the autoantibody is directed to platelets, the resulting platelet destruction can lead to chronic autoimmune thrombocytopenia purpura.

In one embodiment of the present invention, the at least one other specificity of the present therapeutic agent may be directed to the specific binding site of an autoantibody. By directing the other specificity to the specific binding site of the autoantibody, clearance of antibodies with potentially harmful specificities is achieved, while the clearance of useful, normal antibodies is avoided.

In another embodiment, the present therapeutic agent may induce clearance of autoantibodies in the form of an immune complex. In this case, the at least one other specificity of the present therapeutic agent preferably is directed to activated C1q, or activated C3 component, which is bound to the immune complex. Thus, autoantibody clearance may be induced regardless of the epitope recognized by the autoantibody specific binding site. By directing the other specificity only to complement components involved in immune complexes, the clearance and depletion of normal complement components may be avoided. Antibodies that specifically recognize immune complex-bound, activated C1q are described in U.S. Pat. No. 4,595,654, incorporated herein by reference.

Undesirable antibodies may also have specificities against transplanted tissue from other species. For example, porcine organs transplanted into humans typically complex with antibodies present within the human host within hours of transplantation. The host antibodies may activate the complement system, resulting in damage and rejection of the transplanted tissue. Fukushima et al. (1994) Transplantation 57:923; Pruitt et al., (1994) Transplantation 57:363. The major epitope on non-human tissue responsible for transplant rejection is the α-galactosyl epitope (Galα1-3Galβ1-4GlcNAc-R). Galili et al. (1985) J. Exp. Med. 162:573. Up to 1% of all serum IgG in humans recognizes the α-galactosyl epitope. Galili et al. (1984) J. Exp. Med. 160:1519.

It is one objective of the invention to ameliorate the rejection response of humans toward non-human tissue by inducing the clearance of antibodies directed toward transplanted tissue. In accord with this objective, the present therapeutic agent has at least one specificity directed to the specific binding site of an anti-graft antibody, and at least one specificity for Ii. In a preferred embodiment, the specific binding site of an anti-graft antibody recognizes the α-galactosyl epitope. In a more preferred embodiment, the least one specificity for a specific binding site of the anti-graft antibody is a polymer of alpha-galactose.

The chemical constitution of the therapeutic agents may also vary, but they should be capable of specific binding. Accordingly, macromolecule, such as proteins, carbohydrates (e.g., lectins) and RNAs are preferred. Due to the well known ability to generate molecules capable of binding with a wide range of specificities, antibodies and antibody fragments and derivatives are particularly preferred. Both monoclonal and polyclonal antibodies may be prepared according to established methods in the art. Because they bind with a single, defined specificity, monoclonal antibodies are a preferred starting material. Having generated different monoclonal antibodies, and thus a variety different specificities, these starting molecules can be used to generate the multivalent, multispecific agents of the invention. The art is well versed in both recombinant and chemical methods (crosslinking) for generating such agents.

Fragments of antibodies include any portion of the antibody which is capable of binding the target antigen. Antibody fragments specifically include F(ab')$_2$, Fab, Fab' and Fv fragments. These can be generated from any class of antibody, but typically are made from IgG or IgM. They may be made by conventional recombinant DNA techniques or, using the classical method, by proteolytic digestion with papain or pepsin. See CURRENT PROTOCOLS IN IMMUNOLOGY, chapter 2, Coligan et al., eds., (John Wiley & Sons 1991-92).

F(ab')$_2$ fragments are typically about 110 kDa (IgG) or about 150 kDa (IgM) and contain two antigen-binding regions, joined at the hinge by disulfide bond(s). Virtually all, if not all, of the Fc is absent in these fragments. Fab' fragments are typically about 55 kDa (IgG) or about 75 kDa (IgM) and can be formed, for example, by reducing the disulfide bond(s) of an F(ab')$_2$ fragment. The resulting free sulfhydryl group(s) may be used to conveniently conjugate Fab' fragments to other molecules, such as detection reagents (e.g., enzymes).

Fab fragments are monovalent and usually are about 50 kDa (from any source). Fab fragments include the light (L) and heavy (H) chain, variable ($V_L$ and $V_H$, respectively) and constant ($C_L$ and $C_H$, respectively) regions of the antigen-binding portion of the antibody. The H and L portions are linked by an intramolecular disulfide bridge.

Fv fragments are typically about 25 kDa (regardless of source) and contain the variable regions of both the light and heavy chains ($V_L$ and $V_H$, respectively). Usually, the $V_L$ and $V_H$ chains are held together only by non-covalent interacts and, thus, they readily dissociate. They do, however, have the advantage of small size and they retain the same binding properties of the larger Fab fragments. Accordingly, methods have been developed to crosslink the $V_L$ and $V_H$ chains, using, for example, glutaraldehyde (or other chemical crosslinkers), intermolecular disulfide bonds (by incorporation of cysteines) and peptide linkers. The resulting Fv is now a single chain (i.e., SCFv).

One preferred method involves the generation of SCFvs by recombinant methods, which allows the generation of Fvs with new specificities by mixing and matching variable chains from different antibody sources. In a typical method, a recombinant vector would be provided which comprises the appropriate regulatory elements driving expression of a cassette region. The cassette region would contain a DNA encoding a peptide linker, with convenient sites at both the 5' and 3' ends of the linker for generating fusion proteins. The DNA encoding a variable region(s) of interest may be cloned in the vector to form fusion proteins with the linker, thus generating an SCFv.

In an exemplary alternative approach, DNAs encoding two Fvs may be ligated to the DNA encoding the linker, and the resulting tripartite fusion may be ligated directly into a conventional expression vector. The SCFv DNAs generated any of these methods may be expressed in prokaryotic or eukaryotic cells, depending on the vector chosen.

In one embodiment, the agent sought to be cleared is a parasite, such as an leishmania, malaria, trypanosomiasis, babesiosis, or schistosomiasis. In such cases the inventive molecules may be directed against a suitable parasite-associated epitope which includes, but is not limited to, the following.

| Parasite | Epitope | References |
|---|---|---|
| *Plasmodium Falciparum* (Malaria) | (NANP)3 | Good et al. (1986) J. Exp. Med. 164:655 |
| | Circumsporoz. protein AA 326–343 | Good et al. (1987) Science 235:1059 |
| *Leishmania donovani* | Repetitive peptide | Liew et al. (1990) J. Exp. Med. 172:1359 |
| *Leishmani major* | EAEEAARLQA (code) | This application |
| *Toxoplasma gondii* | P30 surface protein | Darcy et al. (1992) J. Immunolog. 149:3636 |
| *Schistosoma mansoni* | Sm-28GST antigen | Wolowxzuk et al. (1991) J. Immunol 146:1987 |

In another embodiment, the agent sought to be cleared is a virus, such as human immunodeficiency virus (HIV), Epstein-Barr virus (EBV), or hepatitis. In such cases, the inventive therapeutic agent may be directed against a suitable viral epitope including, but not limited to:

| Virus | Epitope | Reference |
|---|---|---|
| HIV gp120 | V3 loop, 308–331 | Jatsushita, S. et al. (1988) J. Viro. 62:2107 |
| HIV gp120 | AA 428–443 | Ratner et al. (1985) Nature 313:277 |
| HIV gp120 | AA 112–124 | Berzofsky et al. (1988) Nature 334:706 |
| HIV | Reverse transcriptase | Hosmalin et al. (1990) PNAS USA 87:2344 |
| Flu | nucleoprotein AA 335–349, 366–379 | Townsend et al. (1986) Cell 44:959 |
| Flu | haemagglutinin AA48–66 | Mills et al. (1986) J. Exp. Med. 163:1477 |
| Flu | AA111–120 | Hackett et al. (1983) J. Exp. Med 158:294 |
| Flu | AA114–131 | Lamb, J. and Green N. (1983) Immunology 50:659 |
| Epstein-Barr | LMP43–53 | Thorley-Lawson et al. (1987) PNAS USA 84:5384 |
| Hepatitis B | Surface Ag AA95–109; AA 140–154 | Milich et al. (1985) J. Immunol. 134:4203 |
| | Pre-S antigen AA 120–132 | Milich et al. (1986) J. Exp. Med. 164:532 |
| Herpes simplex | gD protein AA5–23 | Jayaraman et al. (1993) J. Immunol. 151:5777 |
| | gD protein AA241–260 | Wyckoff et al. (1988) Immunobiology 177:134 |
| Rabies | glycoprotein AA32–44 | MacFarlan et al. (1984) J. Immunol. 133:2748 |

The agent sought to be cleared may also be bacterial. In this case, the inventive molecule may have a specificity to a suitable bacterial epitope which includes, but is not limited to:

| Bacteria | Epitope ID | Reference |
|---|---|---|
| *Tuberculosis* | 65Kd protein AA112–126 AA163–184 AA227–243 AA242–266 AA437–459 | Lamb et al. (1987) EMBO J. 6:1245 |
| *Staphylococcus* | nuclease protein AA61–80 | Finnegan et al. (1986) J. Exp. Med. 164:897 |
| *E. coli* | heat stable enterotoxin | Cardenas et al. (1993) Infect. Immunity 61:4629 |
| | heat liable enterotoxin | Clements et al. (1986) Infect. Immunity 53:685 |
| *Shigella sonnei* | form I antigen | Formal et al. (1981) Infect. Immunity 34:746 |

Pharmaceutical Compositions

Pharmaceutical compositions according to the invention comprise at least one therapeutic agent as described above. In addition, these compositions typically further contain a suitable pharmaceutical excipient. Many such excipients are known to the art and examples may be found in REMINGTON'S PHARMACEUTICAL SCIENCES, chapters 83-92, pages 1519-1714 (Mack Publishing Company 1990) (Remington's), which are hereby incorporated by reference. The choice of excipient will, in general, be determined by compatibility with the therapeutic agent(s) and the route of administration chosen. Although the subject compositions are suitable for administration via numerous routes, parenteral administration is generally preferred. The inventive compositions may be formulated as a unit dose which will contain either a therapeutically effective dose or some fraction thereof.

Methods of Preparing Multivalent Molecules

Multivalent, multispecific antibody derivatives can be prepared by a variety of conventional procedures, ranging from glutaraldehyde linkage to more specific linkages between functional groups. The antibodies and/or antibody fragments are preferably covalently bound to one another, directly or through a linker moiety, through one or more functional groups on the antibody or fragment, e.g., amine, carboxyl, phenyl, thiol, or hydroxyl groups. Various conventional linkers in addition to glutaraldehyde can be used, e.g., disiocyanates, diiosothiocyanates, bis(hydroxysuccinimide) esters, carbodiimides, maleimidehydroxy-succinimde esters, and the like. The optimal length of the linker may vary according to the type of target cell. The most efficacious linker size can be determined empirically by testing (and ensuring) reactivity to both target and Ii. Such immunochemical techniques are well known.

A simple method to produce multivalent antibodies is to mix the antibodies or fragments in the presence of glutaraldehyde. The initial Schiff base linkages can be stabilized, e.g., by borohydride reduction to secondary amines. A diiosothiocyanate or carbodiimide can be used in place of glutaraldehyde as a non-site-specific linker.

The simplest form of a multivalent, multispecific antibody is a bispecific antibody comprising binding specificities both to a target agent to be cleared and to Ii. Bispecific antibodies can be made by a variety of conventional methods, e.g., disulfide cleavage and reformation of mixtures of whole IgG or, preferably F(ab')$_2$ fragments, fusions of more than one hybridoma to form polyomas that produce antibodies having more than one specificity, and by genetic-engineering. Bispecific antibodies have been prepared by oxidative cleavage of Fab' fragments resulting from reductive cleavage of different antibodies. This is advantageously carried out by mixing two different F(ab')$_2$ fragments produced by pepsin digestion of two different antibodies, reductive cleavage to form a mixture of Fab' fragments, followed by oxidative reformation of the disulfide linkages to produce a mixture of F(ab')$_2$ fragments including bispecific antibodies containing a Fab' portion specific to each of the original epitopes (i.e., target and Ii). General techniques for the preparation of multivalent antibodies may be found, for example, in Nisonhoff et al., Arch Biochem. Biophys. 93: 470 (1961), Hammerling et al., J. Exp. Med. 128: 1461 (1968), and U.S. Pat. No. 4,331,647.

More selective linkage can be achieved by using a heterobifunctional linker such as maleimide-hydroxysuccinimide ester. Reaction of the ester with an antibody or fragment will derivatize amine groups on the antibody or fragment, and the derivative can then be reacted with, e.g., an antibody Fab fragment having free sulfhydryl groups (or, a larger fragment or intact antibody with sulfhydryl groups appended thereto by, e.g., Traut's Reagent). Such a linker is less likely to crosslink groups in the same antibody and improves the selectivity of the linkage.

It is advantageous to link the antibodies or fragments at sites remote from the antigen binding sites. This can be accomplished by, e.g., linkage to cleaved interchain sulfydryl groups, as noted above. Another method involves reacting an antibody having an oxidized carbohydrate portion with another antibody which has at lease one free amine function. This results in an initial Schiff base (imine) linkage, which is preferably stabilized by reduction to a secondary amine, e.g., by borohydride reduction, to form the final product. Such site-specific linkages are disclosed, for small molecules, in U.S. Pat. No. 4,671,958, and for larger addends in U.S. Pat. No. 4,699,784.

The interchain disulfide bridges of the an F(ab')$_2$ fragment having target specificity are gently reduced with cysteine, taking care to avoid light-heavy chain linkage, to form Fab'-SH fragments. The SH group(s) is(are) activated with an excess of bis-maleimide linker (1,1'-(methylenedi-4,1-phenylene)bis-malemide). An Ii-specific Mab, such as LL1, is converted to Fab'-SH and then reacted with the activated target-specific Fab'-SH fragment to obtain a bispecific antibody.

Alternatively, such bispecific antibodies can be produced by fusing two hybridoma cell lines that produce anti-target Mab and anti-Ii Mab. Techniques for producing tetradomas are described, for example, by Milstein et al., Nature 305: 537 (1983) and Pohl et al., Int. J. Cancer 54: 418 (1993).

Finally, such bispecific antibodies can be produced by genetic engineering. For example, plasmids containing DNA coding for variable domains of an anti-target Mab can be introduced into hybridomas that secrete LL1 antibodies. The resulting "transfectomas" produce bispecific antibodies that bind target and Ii. Alternatively, chimeric genes can be designed that encode both anti-target and anti-Ii binding domains. General techniques for producing bispecific antibodies by genetic engineering are described, for example, by Songsivilai et al., Biochem. Biophys. Res. Commun. 164: 271 (1989); Traunecker et al., EMBO J. 10: 3655 (1991); and Weiner et al., J. Immunol. 147: 4035 (1991).

A higher order multivalent, multispecific molecule can be obtained by adding various antibody components to a bispecific antibody, produced as above. For example, a bispecific antibody can be reacted with 2-iminothiolane to introduce one or more sulfhydryl groups for use in coupling the bispecific antibody to an further antibody derivative that binds an the same or a different epitope of the target antigen, using the bis-maleimide activation procedure described above. These techniques for producing multivalent antibodies are well known to those of skill in the art. See, for example, U.S. Pat. No. 4,925,648, and Goldenberg, international publication No. WO 92/19273, which are incorporated by reference.

Methods of Treatment

The methods of the invention typically involve administering to a patient in need of treatment a therapeutically effective amount of a composition which comprises a therapeutic agent of the invention. The patient is usually human, but may be a non-human animal. A patient will be in need of treatment where it is desirable to induce clearance of a target agent. A therapeutically effective amount is generally an amount sufficient to accelerate clearance of the target agent versus a control.

Some methods involve the use of the instant therapeutic agents to induce clearance of cytoreductive agents (chemotherapeutic agents). In a typical method, a patient is treated with a cytoreductive agent, then the excess cytoreductive agent is removed by administration of an inventive compound having at least one specificity for the cytoreductive agent. In one exemplary method, the cytoreductive agent comprises an antibody for targeting and the inventive compound has a specificity for the antibody portion of the agent. In this manner, any portion of the cytoreductive agent that fails to specifically interact with its target is removed. It is anticipated that this method will allow the use of higher, more effective doses of the cytoreductive agent. Side effects will be minimized because the inventive compounds induce clearance of any excess.

Other methods involve reducing the background caused by excess non-localizing diagnostic agents. These methods are useful, for example, in an imaging procedure where a targeting agent (e.g., an antibody) is conjugated with a detectable marker (e.g., a radionuclide). In a typical method, the diagnostic agent would be administered to a patient and, following administration but before detection, an inventive compound having at least one specificity for the diagnostic agent and at least one specificity for Ii is provided to the patient, thereby inducing clearance of the excess diagnostic.

Still other methods involved the clearance of pathogens, such as bacteria, from the patient. It is envisioned that this approach will have particular benefit for patients who have become septic. Typically, these methods involve administering an inventive compound having at least one specificity for a pathogen of interest (e.g., endotoxin) and at least one specificity for Ii, thereby inducing clearance of the pathogen.

The term "treating" in its various grammatical forms in relation to the present invention refers to preventing, curing, reversing, attenuating, alleviating, minimizing, suppressing or halting the deleterious effects of a disease state, disease progression, disease causative agent (e.g., bacteria or viruses) or other abnormal condition. Because some of the inventive methods involve the physical removal of the etiological agent, the artisan will recognize that they are equally effective in situations where the inventive compound is administered prior to, or simultaneous with, exposure to the etiological agent (prophylactic treatment) and situations where the inventive compounds are administered after (even well after) exposure to the etiological agent.

EXAMPLES

Example 1

This example provides an illustrative method for making and using an inventive compound to reduce the background in a radioimmunotherapy application. Numerous monoclonal antibodies directed against tumor associated antigens (TAA) are now being evaluated as radioimmunotherapy agents. In many instances the antigen is shed into the blood, and it is necessary to administer large doses of unlabeled antibody to complex the blood antigen, prior to, or with the administration of the radiolabeled antibody. An LL1-anti-TAA MAb can be used to clear the antigen rapidly from the blood. In the preferred mode, the anti-TAA MAb is directed to a different, spatially separated epitope on the TAA-molecule, from the epitope on the TAA-molecule targeted by the therapeutic MAb.

NP-3 is an antibody that reacts with an epitope on CEA that is spatially separate from the epitope reactive with the antibody to be used for radiotherapy, hMN14. hMN14 is a "humanized" antibody that has been constructed by grafting the complementarity-determining region (cdr) of MN14 MAb to a human immunoglobulin lacking an endogenous cdr. A bispecific LL1-NP-3 MAb is constructed by conventional chemistry. The interchain disulfide bridges of an NP-3-derived F(ab')$_2$ fragment are gently reduced with cysteine, taking care to avoid light-heavy chain linkage, to form Fab'-SH fragments. The SH group(s) is(are) activated with an excess of bis-maleimide linker (1,1'-(methylenedi-4,1-phenylene)bis-malemide). The LL1 Mab is converted to Fab'-SH and then reacted with the activated NP-3 Fab'-SH fragment to obtain the bispecific antibody.

A patient with colon carcinoma having a plasma CEA concentration of 10 µg/ml is treated with $^{131}$I-hMN14. Twenty four hours prior to treatment, 20 mg of bispecific MAb LL1-NP-3 is administered to the patient. At the time of administration of $^{131}$I-hMN14, a heat-extraction CEA-EIA (Hansen et al., Clinical Chemistry, 35, 146-151, 1989) demonstrates the blood CEA concentration is less than 100 ng/ml. The radiolabeled antibody is observed, and radioimmunoscintigrapy demonstrates intense targeting of the tumor.

Example 2

This example provides an illustrative method for inducing clearance of excess non-tumor bound immunotherapeutic. Bispecific antibodies can be used for indirect targeting of a radiolabeled chelate to a cancer (Faivre-Chauvet A. et al., Nuclear Med Communications 17:781-789 (1996.) Rapid elimination of excess, non-tumor-targeted antibody from the blood and lymphatic fluid is required to obtain optimal tumor targeting. This can be accomplished with a LL1-anti-Id bispecific antibody.

A bispecific antibody (hMN14/TTIN1 (Kranenborg MGGC et al., Cancer Research 55:5864-5867 (1995) as the anti-chelate binding Fab. A second bispecific antibody (LL1/WI2) is concentrated using a Fab from LL1 and a Fab from WI2; WI2 is a anti-Id-Mab raised to MN14.

Radioscintigraphy with CEA-Scan demonstrates that a patient with a previous treated thyroid cancer and a rising CEA titer has numerous metastatic sites of disease. One hundred mg of the hMN14/TTIN1 bispecific MAb radiolabeled with 5 mCi $^{131}$I MAb is infused into the patient. Radioscintigraphy performed 48 hours later demonstrates positive tumor targeting, and assay of the blood radioactivity demonstrates a blood antibody concentration of 2% injected dose per liter. Twenty mg of LL1/WI2 bispecific antibody is then infused into the patient, and blood radioactivity monitored for 24 hours. Rapid disappearance of the labeled antibody from the blood is observed, with the percent injected dose of intact antibody per liter of blood being less than 0.1% after 24 hours. At this time, 50 mCi of $^{90}$Y-chelate mixed with 5 mCi of $^{111}$I-chelate is infused. Interpolation of radioscintigraphy scans of the radiolabeled indium localized in the tumor and marrow demonstrates that the radiolabeled yttrium delivered 5000-8000 rads to the thyroid cancer deposits, with less than 300 rads delivered to the bone marrow. Minimal toxicity is observed, and a complete tumor remission if attained.

Example 3

This example provide a method for increasing the therapeutic benefit of an two-step immunotherapeutic by eliminating excess non-binding primary agent. In the case of WI2-LL1 as clearing agent for hMN14, the WI2 binds to circulating hMN14 and to recruited cells expressing surface invariant chain (Ii), thus neutralizing circulating hMN14 by phagocytosis. When the hMN14 carries a secondary targeting site, such as biotin or streptavidin, that second site is removed from circulation simultaneously by virtue of its internalization. This type of blocking is advantageous in that one is not depositing excess hMN14-biotin (streptavidin) in an single organ, the liver, where it could form a sink for subsequently injected streptavidin (biotin) conjugates or radioconjugates.

A patient with a carcinoembryonic antigen (CEA)-expressing cancer is treated with a dose of hMN14 substituted with a molar equivalent of streptavidin, in an amount up to that which is sufficient to saturate available CEA in the tumor. A period of time is allowed for this to happen (typically 24-96 h). Optionally, the administered hMN14-streptavidin is given along with a tracer amount of radiolabeled hMN14-streptavidin, the intent being to use said radiolabel for imaging tumor localization and/or serum clearance of the hMN14-streptavidin. Either test is well known in the art. At, or near, the time of maximum tumor accretion the patient is treated with sufficient WI2×LL1 bispecific antibody to ensure complete binding of the antiidiotypic arm (WI2) to hMN14 remaining in the circulation. Once bound to hMN14, sufficient time is allowed for the LL1 arm of the bispecific MAb to recruit cells expressing surface HLA class II invariant chain (such as macrophages) to the hMN14-streptavidin/WI2xLL1 complex to be internalized by the phagocytic cell. Once residual hMN14-streptavidin has been removed from the circulation the patient is injected with radiolabeled biotin, which is thus free to bind to the remaining available streptavidin sites in the body. These are primarily on tumors.

A patient with metastatic breast cancer is treated with five hundred milligrams of hMN14-streptavidin radiolabeled with ten milliCuries of I-131-MN14-streptavidin. After seventy-two hours the patient is treated with one gram of WI2xLL1. An additional forty-eight hours later sites of disease are confirmed using single photon emission computed tomography, and the patient is given one hundred milliCuries of biotin-D-Ala-D-Lys(Bi-212-DOTA)-D-Lys(biotin)-NH$_2$. Six hours later the patient is retreated with a further one hundred milliCuries of biotin-D-Ala-D-Lys(Bi-212-DOTA)-D-Lys(biotin)NH$_2$. Subsequent to treatment all tumors regress.

Example 4

A patient with CEA-positive ovarian cancer is treated with five hundred milligrams of MN-14-streptavidin radiolabeled with three hundred milliCuries of I-131-MN14-streptavidin. After forty-eight hours the patient is treated with two grams of WI2xLL1. After a further eight hours a 500 milliCurie dose of biotin-D-Tyr.-D-Lys(Y-90-DOTA)NH$_2$ is given. Both iodine-131 and yttrium-90 delivered specifically to sites of disease act together to shrink and destroy tumors in the patient.

The foregoing detailed description and examples are merely illustrative of the invention and are not meant to be limiting in any way. The artisan will immediately recognize further embodiments that are within the scope of the present invention.

What is claimed is:

1. A bispecific antibody or fragment thereof having a specificity for a tumor associated antigen (TAA) and a specificity for the ULA class II invariant chain (Ii).

2. A bispecific antibody or fragment thereof having at least one binding site for the HLA class II invariant chain and at least one binding site for a tumor associated antigen (TAA) selected from the group consisting of CBA (carcinoembryonic antigen), alphafetoprotein (AFP), human chorionic gonadotropin (HCG), colon-specific antigen-p (CSAp), prostatic acid phosphatase, pancreatic oncofetal antigen (POA), placental alkaline phosphatase, pregnancy beta$_1$-globulin, parathormone, calcitonin, tissue polypeptide antigen, T-antigen, beta$_2$-microglobulin, mammary tumor-associated glycoproteins (MTGP), galactosyl transferase-II (GT-II), gp-52 viral-associated antigen, basic fetoprotein (BFP), terminal deoxynucleotidyl transferase (TdT), cytoplasmic melanoma-associated antigens, human astrocytoma-associated antigen (HAAA), common glioma antigen (CGA), glioembryonic antigen (GEA), glial fibrillary acidic protein (GFA), common meningioma antigen (CMA), ferritin, tumor angiogenesis factor (TAF), ovarian cystadenocarcinoma-associated antigen (OCCA), ovarian tumor-specific antigen (OCA) and cervical cancer antigens (CA-58, CCA, TA-4).

3. The bispecific antibody of claim 2, wherein the TAA is CEA.

4. The bispecific antibody of claim 2, wherein the TAA is AFP.

5. The bispecific antibody of claim 2, wherein the TAA is HCG.

6. The bispecific antibody of claim 2, wherein the TAA is CSAp.

7. The bispecific antibody of claim 2, wherein the TAA is prostatic acid phosphatase.

8. The bispecific antibody of claim 2, wherein the TAA is GT-II.

9. The bispecific antibody of claim 2, wherein the TAA is TdT.

\* \* \* \* \*

SEQUENCE LISTING

<160> NUMBER OF SEQ ID NOS: 2

<210> SEQ ID NO 1
<211> LENGTH: 12
<212> TYPE: PRT
<213> ORGANISM: Plasmodium falciparum

<400> SEQUENCE: 1

Asn Ala Asn Pro Asn Ala Asn Pro Asn Ala Asn Pro
 1               5                   10

<210> SEQ ID NO 2
<211> LENGTH: 10
<212> TYPE: PRT
<213> ORGANISM: Leishmania major

<400> SEQUENCE: 2

Glu Ala Glu Glu Ala Ala Arg Leu Gln Ala
 1               5                   10

UNITED STATES PATENT AND TRADEMARK OFFICE
CERTIFICATE OF CORRECTION

PATENT NO. : 7,230,084 B2 Page 1 of 1
APPLICATION NO. : 10/259853
DATED : June 12, 2007
INVENTOR(S) : Hans J. Hansen It is certified that error appears in the above-identified patent and that said Letters Patent is hereby corrected as shown below:

Col. 14, line 4, please replace "ULA" with --HLA--.

Col. 14, line 8, please replace "CBA" with --CEA--.

Signed and Sealed this

Fourth Day of September, 2007

JON W. DUDAS
*Director of the United States Patent and Trademark Office*